US005652216A

United States Patent [19]
Kornfelt et al.

[11] Patent Number: 5,652,216
[45] Date of Patent: Jul. 29, 1997

[54] PHARMACEUTICAL PREPARATION

[75] Inventors: Troels Kornfelt, Virum; Henrik Rasmussen, Copenhagen; Flemming Steen Jensen, Alleroed, all of Denmark

[73] Assignee: Novo Nordisk A/S, Bagsvaerd, Denmark

[21] Appl. No.: 275,855

[22] Filed: Jul. 15, 1994

[30] Foreign Application Priority Data

May 26, 1994 [DK] Denmark .................................. 0590/94

[51] Int. Cl.$^6$ .................................................. A61K 38/26
[52] U.S. Cl. ................................................................ 514/12
[58] Field of Search .................................................. 514/12

[56] References Cited

U.S. PATENT DOCUMENTS 4,826,763  5/1989  Norris et al. ............................. 435/68
5,023,088  6/1991  Wong ...................................... 424/473
5,059,587  10/1991  Yamamoto .............................. 514/12

FOREIGN PATENT DOCUMENTS

WO93/12811  7/1993  WIPO .

OTHER PUBLICATIONS

The Merck Index, 10th Edition, Monograph No. 4307, (1983).

*Primary Examiner*—Peter O'Sullivan
*Attorney, Agent, or Firm*—Steve T. Zelson, Esq.; Valeta A. Gregg, Esq.

[57] ABSTRACT

The present invention relates to a pharmaceutical preparation comprising glucagon and a stabilizing amount of a pharmaceutically acceptable ampholyte, especially an amino acid or dipeptide or a mixture thereof and optionally an excipient.

The preparation is stable for extended periods of time in solution at room temperature.

13 Claims, 9 Drawing Sheets

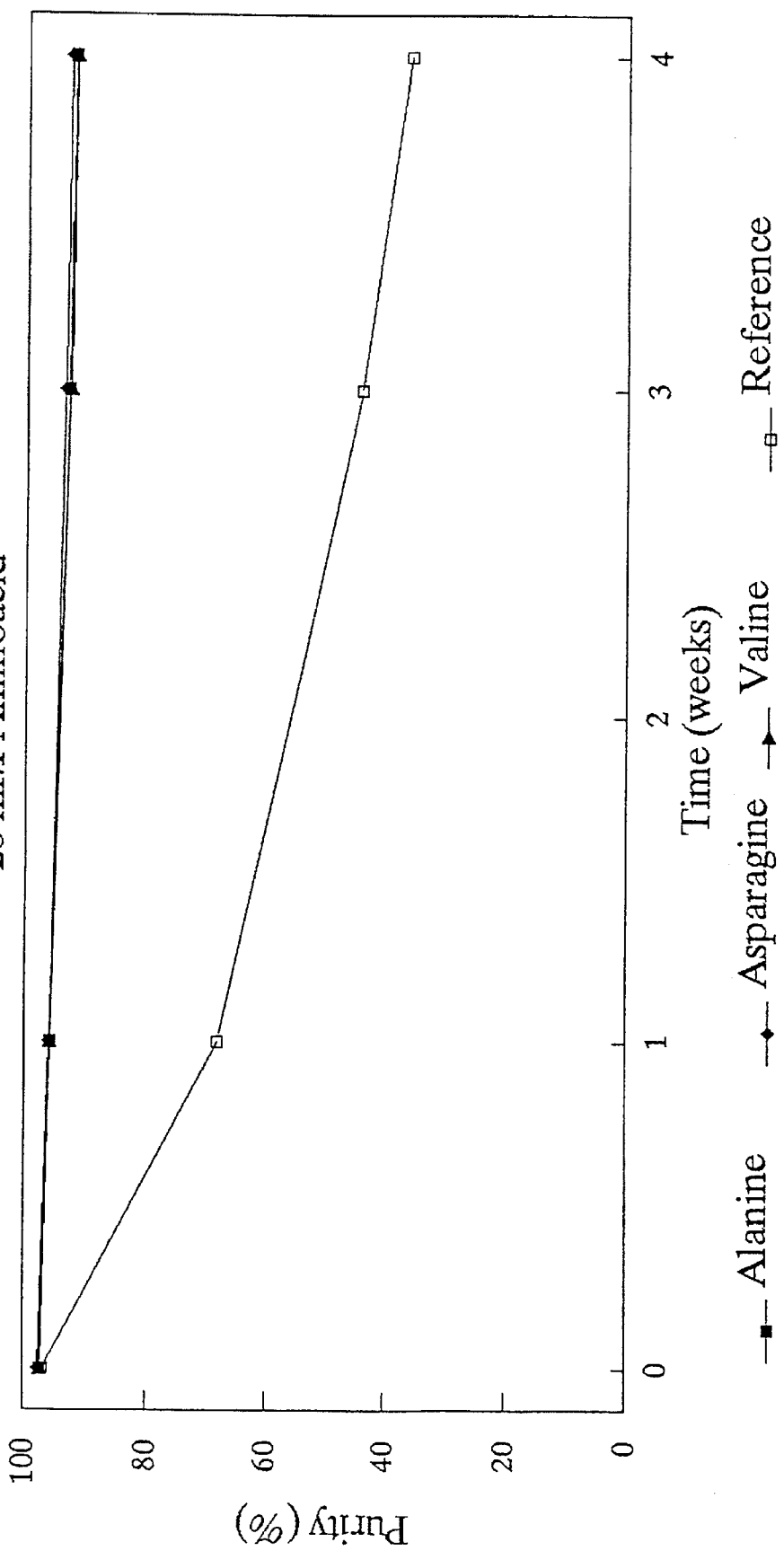

5,652,216

PHARMACEUTICAL PREPARATION

FIELD OF THE INVENTION

The present invention relates to a stabilized pharmaceutical preparation comprising glucagon.

BACKGROUND OF THE INVENTION

Human glucagon is a polypeptide hormone secreted by α-cells of the pancreatic islets of Langerhans. It is a single-chain polypeptide consisting of 29 amino acid residues the sequence of which is published inter alia in The Merck Index, 10 th Edition (1983), Monograph No.4307.

Glucagon is used for the treatment of hypoglycemia in diabetics due to its glycogenolytic effect on the liver. Glucagon also exerts a spasmolytic effect on smooth muscles which is used clinically in connection with several imaging procedures, especially radiology.

Glucagon is at present marketed in the form of a lyophilized product for injection comprising lactose as the sole excipient. The lyophilisate is to be reconstituted using a suitable diluent.

In the production of those conventional pharmaceutical preparations comprising glucagon, utmost care must be taken in order to avoid undesired decomposition of the glucagon during preparation, dispensing and lyophilization. Furthermore, glucagon undergoes decomposition during storage of the finished product at room temperature significantly limiting the shelf-time of the preparation.

Thus, there is a need for a more stable formulation of glucagon retaining its activity for extended periods of time at room temperature. Such stabilized preparations comprising glucagon are desirable for emergency treatment of acute hypoglycemia rendering it possible for diabetic patients to carry a dose of glucagon in their hand bag enabling themselves or another person present to treat an incidence of hypoglycemia immediately.

BRIEF DESCRIPTION OF THE INVENTION

The present invention relates to a stabilized pharmaceutical parenteral preparation comprising glucagon.

BRIEF DESCRIPTION OF THE DRAWINGS

The invention is further explained with reference to the drawings in which

FIG. 9 shows the decomposition of glucagon stabilized with 20 mM Alanine, Asparagine or Valine as compared with the corresponding formulation without addition of amine acid as a function of time.

DETAILED DESCRIPTION OF THE INVENTION

Figure 1:
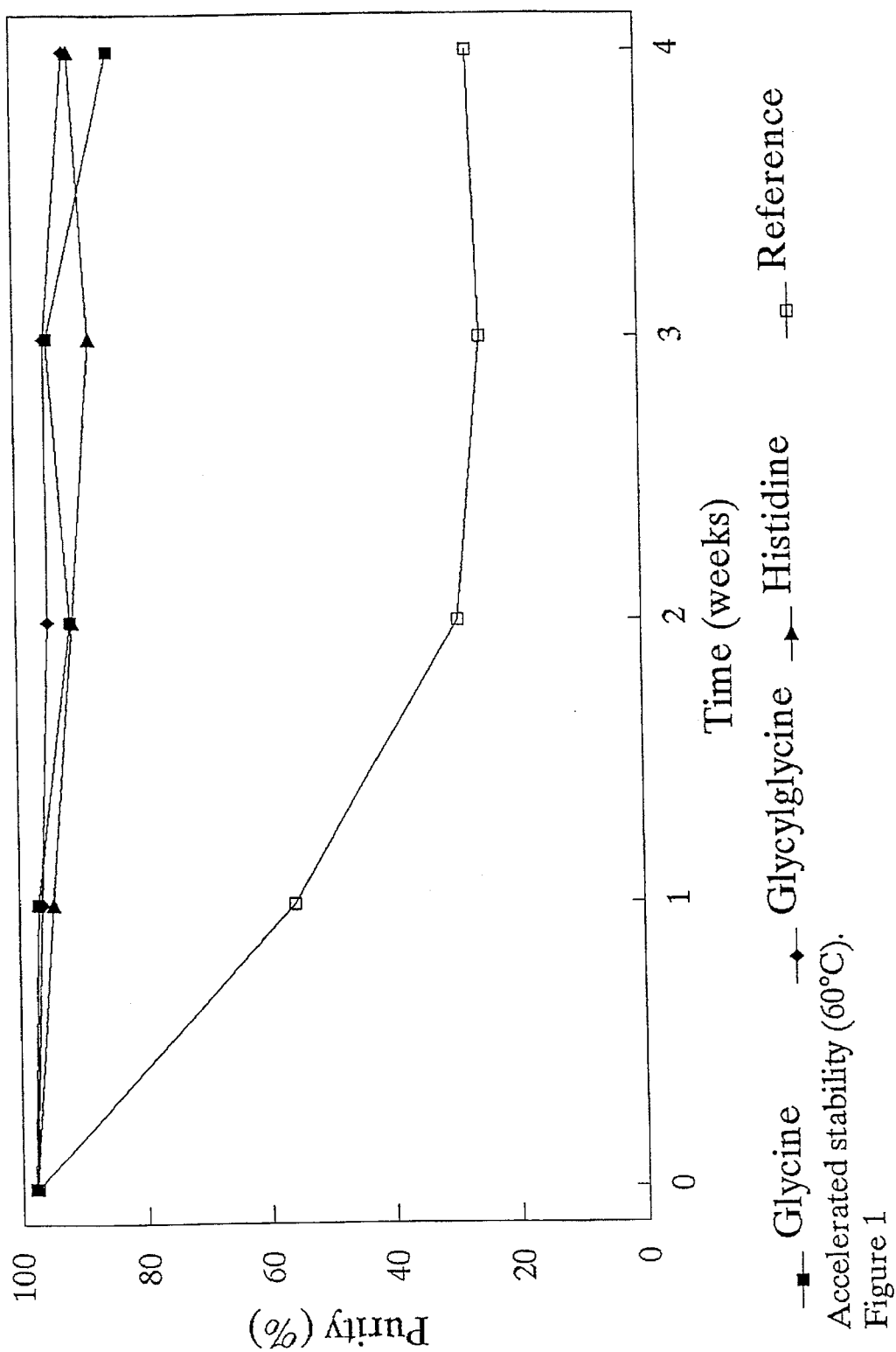
FIG. 1 shows the decomposition of glucagon stabilized with 5 mM Glycine, Glycylglycine or Histidine as compared with the corresponding formulation without addition of amine acid as a function of the time.

The invention relates to a stabilized pharmaceutical preparation comprising glucagon and a stabilizing amount of a pharmaceutically acceptable ampholyte, especially an amino acid or dipeptide or a mixture thereof and optionally an excipient. Such preparations retain the glucagon activity at room temperature, e.g. 25° C., for extended periods of time.

A pharmaceutically acceptable ampholyte to be used in accordance with the invention may be selected from the group consisting of amino acids or derivations thereof such as glycine, ethylglycine (sarcosine), trimethylglycine (betaine), alanine, β-alanine, valine, leucine, nor-leucine, isoleucine, serine, threonine, aspartic acid, glutamic acid, hydroxyglutamic acid, lysine, hydroxylysine, ornithine, arginine, histidine, methionine, asparagine and glutamine; dipeptides such as glycylglycine; pharmaceutically acceptable sulfonic acids or derivatives thereof such as taurine; creatinine, and ethylenediaminetetraacetic acid (EDTA).

An amino acid to be used in accordance with the present invention is preferably a naturally occurring alpha amino acid. Such amino acids may be 1 or d amino acids or a mixture thereof.

Preferably glycine, glycylglycine, histidine or a mixture of two or more of these is used.

A pharmaceutical preparation of the invention in lyophilized form preferably also comprises an excipient, e.g. for facilitating the lyophilization and rapid and complete redissolution thereof when reconstituting the preparation before use.

An excipient may be selected from disaccharides such as lactose, trehalose, and sucrose, sugar alcohols such as sorbitol or mannitol, polysaccharides such as the polymers commercialized as Dextran® products such as Dextran® 40, Dextran® 70 or Dextran® 75, and Ficoll® and polyvalent alcohols such as polyethylene glycol or polyvinyl alcohol or a combination of two or more of these.

The excipient is preferably present in an amount of from 10 to 600 micromoles per mg glucagon giving an optimum stabilization. The excipient preferred according to the invention is lactose.

In a further aspect of the invention, the pharmaceutical preparation of the invention is in the form of a stabilized solution of glucagon.

In order to obtain the desired stabilization, the stabilizing amino acid or dipeptide may be present in an amount from 0.01 to 50 micromoles per mg glucagon. The amount of stabilizing amino acid or dipeptide present per dose of pharmaceutical preparation comprising glucagon is according to the invention from 0.1 to 50 micromoles.

A preferred preparation of the invention comprises glycine, histidine or glycylglycine in an amount about 10 micromoles per mg glucagon. The amount of glycine, histidine or glycylglycine is preferably about 10 micromoles per dose.

The pH of the preparations according to the invention in the form of a solution is preferably adjusted to the interval 1–7. Preferably, the pH is adjusted to the interval 2–4, and most preferred to about 2.8.

The invention also relates to a method for the preparation of a pharmaceutical preparation comprising glucagon and a stabilizing amount of a pharmaceutically acceptable ampholyte wherein glucagon is dissolved in a solution of the ampholyte and optional excipient and lyophilized, optionally after sterile filtration.

The dissolution of the glucagon is preferably carried out at a temperature of from 4° to 8° C.

A most preferred preparation according to the invention comprises glucagon, lactose or mannitol as excipient and glycine, histidine or glycylglycine or a mixture of two or more of these as a stabilizing agent. Such a preparation shows a buffer effect at pH about 2.8 giving a minimum for the rate of decomposition of glucagon. Thus, the invention enables the formulation of a preparation in which glucagon is stable at room temperature.

The amino acid sequence of human glucagon is identical to the amino acid sequence of porcine and bovine glucagon. Hence, glucagon may be isolated by conventional extraction form porcine or bovine pancreatic glands. In the alternative, glucagon may be prepared by fully or partially chemical synthesis or by recombinant techniques, e.g. as disclosed in U.S. Pat. No. 4,826,763.

The pharmaceutical preparations of the invention may be formulated for administration in any suitable way, e.g. by parenteral or oral administration or administration to a mucosal membrane, e.g. nasal administration. The pharmaceutical preparation may be preserved in the form of a dose comprised in a vial or cartridge or any other suitable container.

The invention is explained more in detail in the below Examples which illustrate the invention. They are not to be considered as limiting the scope of the invention being defined by the appended claims.

MATERIALS AND METHODS

Preparation and lyophilization of formulations comprising glucagon was carried out using the following procedure:

Glucagon: Recombinant glucagon prepared in saccharomyces cerivisiae as disclosed in U.S. Pat. No. 4,826,763.

10.7 g lactose and the amino acid or dipeptide was dissolved in approximately 75 ml of distilled water and the pH was adjusted to 2.6–3.0 using 1N hydrochloric acid/sodium hydroxide. The volume was adjusted to 100 ml and the solution was cooled to 4°–8° C. in a refrigerator.

110 mg glucagon was dissolved in the solution and the pH adjusted to pH 2.6–3.0 using 1N hydrochloric acid (maintaining the solution at 4°–8° C.).

The solution was sterile filtered through a 0.2 μm filter (using a 50 cc syringe) and divided into vials, 1 ml in each.

The solution was lyophilized in total 36 hours, using the following procedure:

Prefreezing at −45° C. for 3–5 hours, primary drying from −45° C. to 20° C. and a pressure of 0.1 hPa for 29 hours, and Secondary drying at 20° C. (and full vacuum) for 4 hours using a Heto CD8 apparatus.

EXAMPLES

EXAMPLE 1

Preparation of formulations comprising glucagon, lactose and an amino acid or a dipeptide.

In an analogous manner as described above formulations were prepared from glucagon, lactose and an amino acid or a dipeptide.

As reference was used a formulation comprising glucagon and lactose prepared as described above.

Formulations having the following compositions per vial were prepared:

| Reference: | |
| --- | --- |
| Glucagon | 1.1 mg |
| Lactose USP/Ph Eur | 107 mg |
| 1N HCl | ad pH 2.8 |
| Test formulations: | |
| Glucagon | 1.1 mg |
| Lactose USP/Ph Eur | 107 mg |
| Ampholyte | 5, 10, 20 mM |
| HCl/NaOH | ad pH 2.8 |

The ampholytes tested were:

| | Formulation |
| --- | --- |
| A1 | Glycine |
| A2 | Glycylglycine |
| A3 | Histidine |
| A4 | Aspartic acid |
| A5 | Glutamic acid |
| A6 | Leucine |
| A7 | Alanine |
| A8 | Asparagine |
| A9 | Valine |

Figure 2:
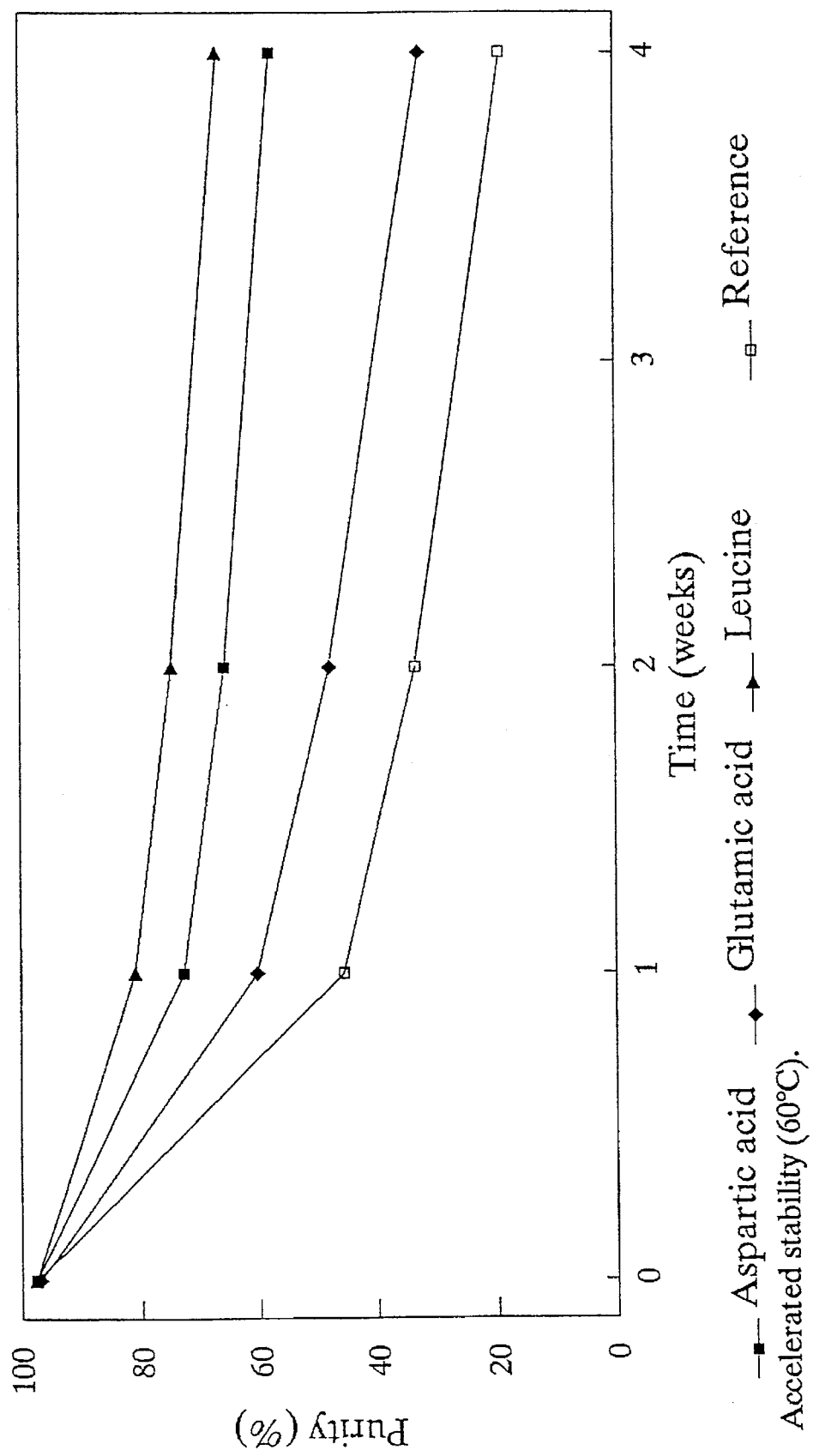
FIG. 2 shows the decomposition of glucagon stabilized with 5 mM Aspartic Acid, Glutamic Acid or Leucine as compared with the corresponding formulation without addition of amine acid as a function of the time.
Figure 3:
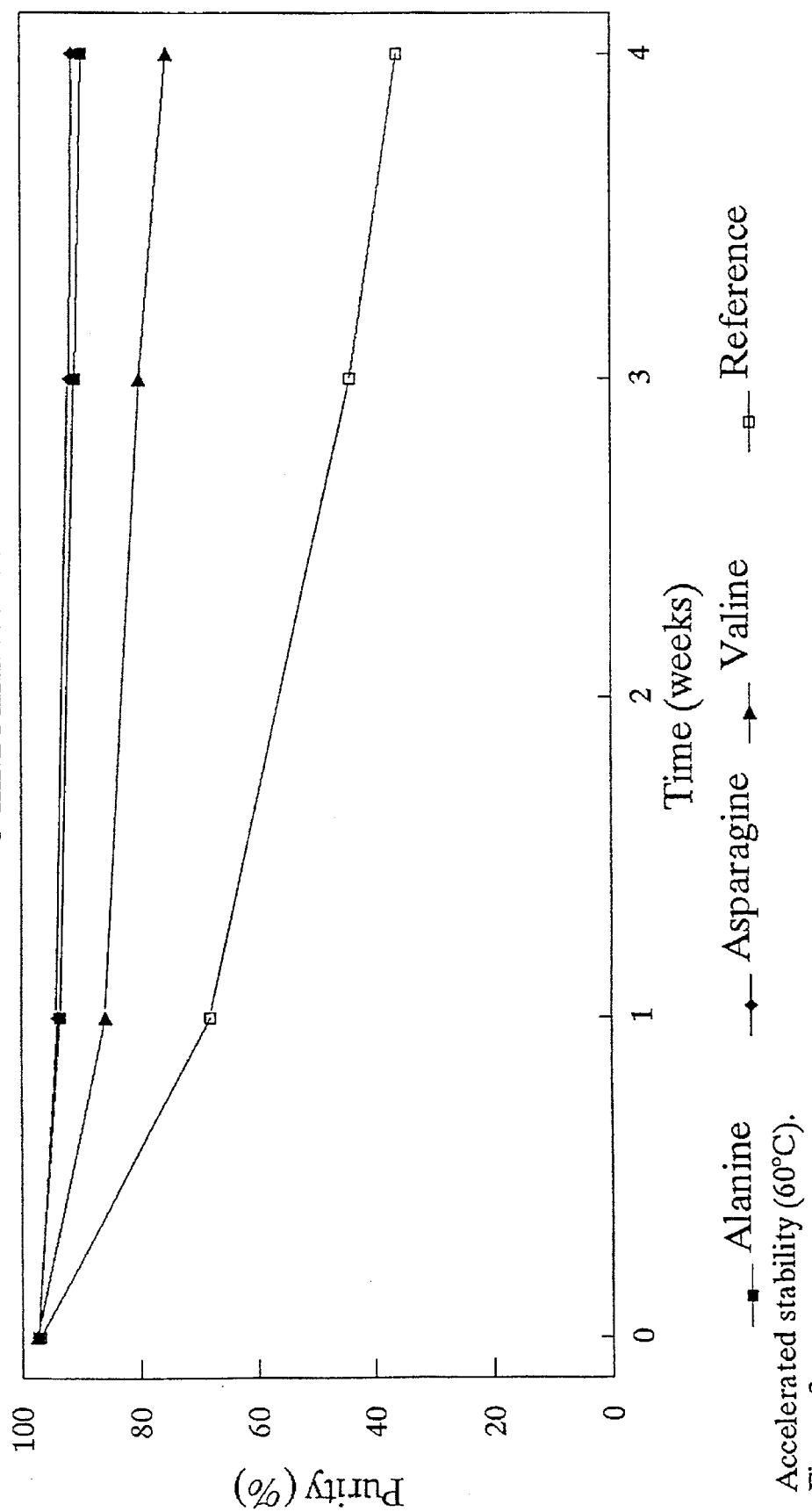
FIG. 3 shows the decomposition of glucagon stabilized with 5 mM Alanine, Asparagine or Valine as compared with the corresponding formulation without addition of amine acid as a function of the time.
Figure 4:
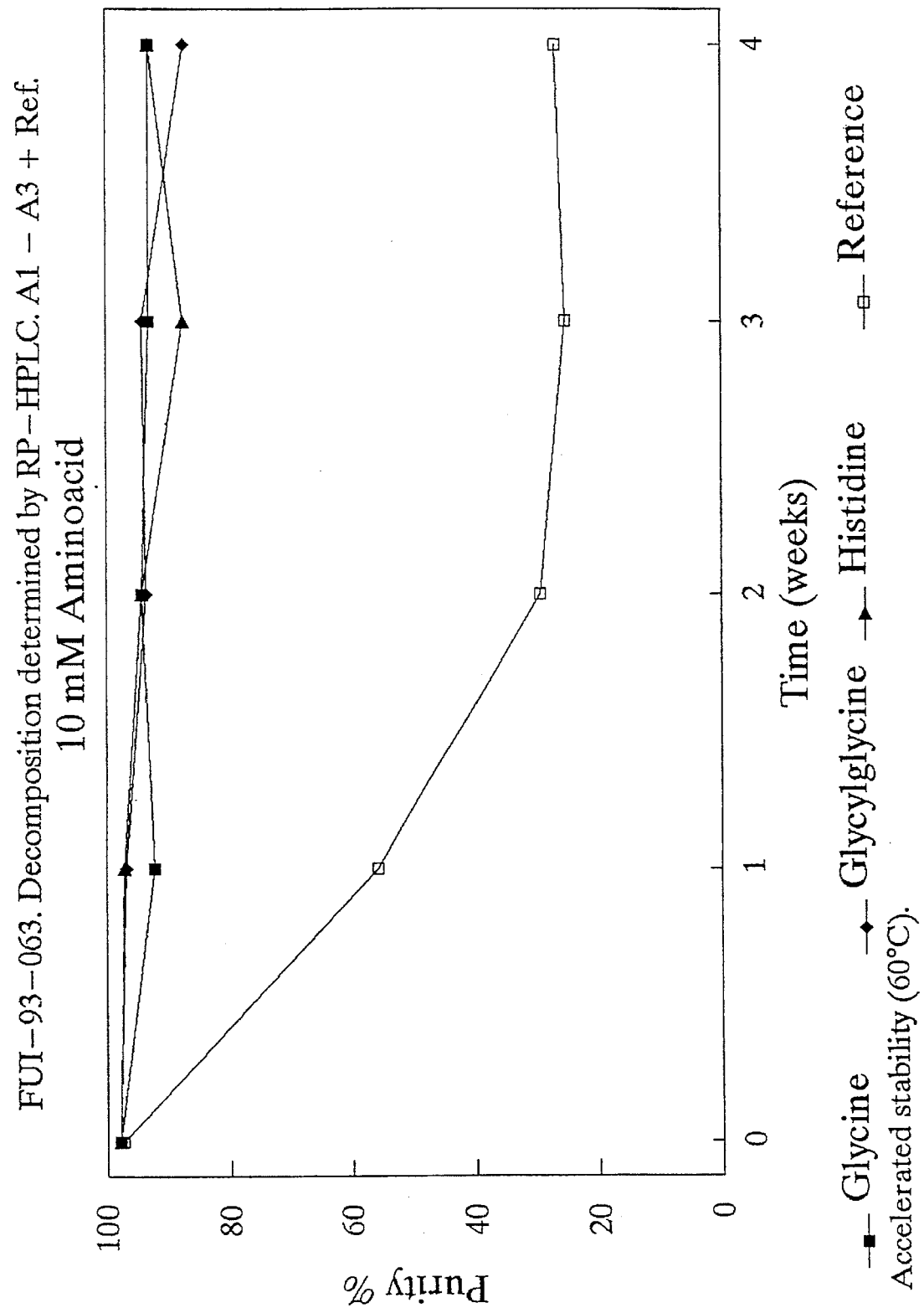
FIG. 4 shows the decomposition of glucagon stabilized with 10 mM Glycine, Glycylglycine or Histidine as compared with the corresponding formulation without addition of amine acid as a function of the time.
Figure 5:
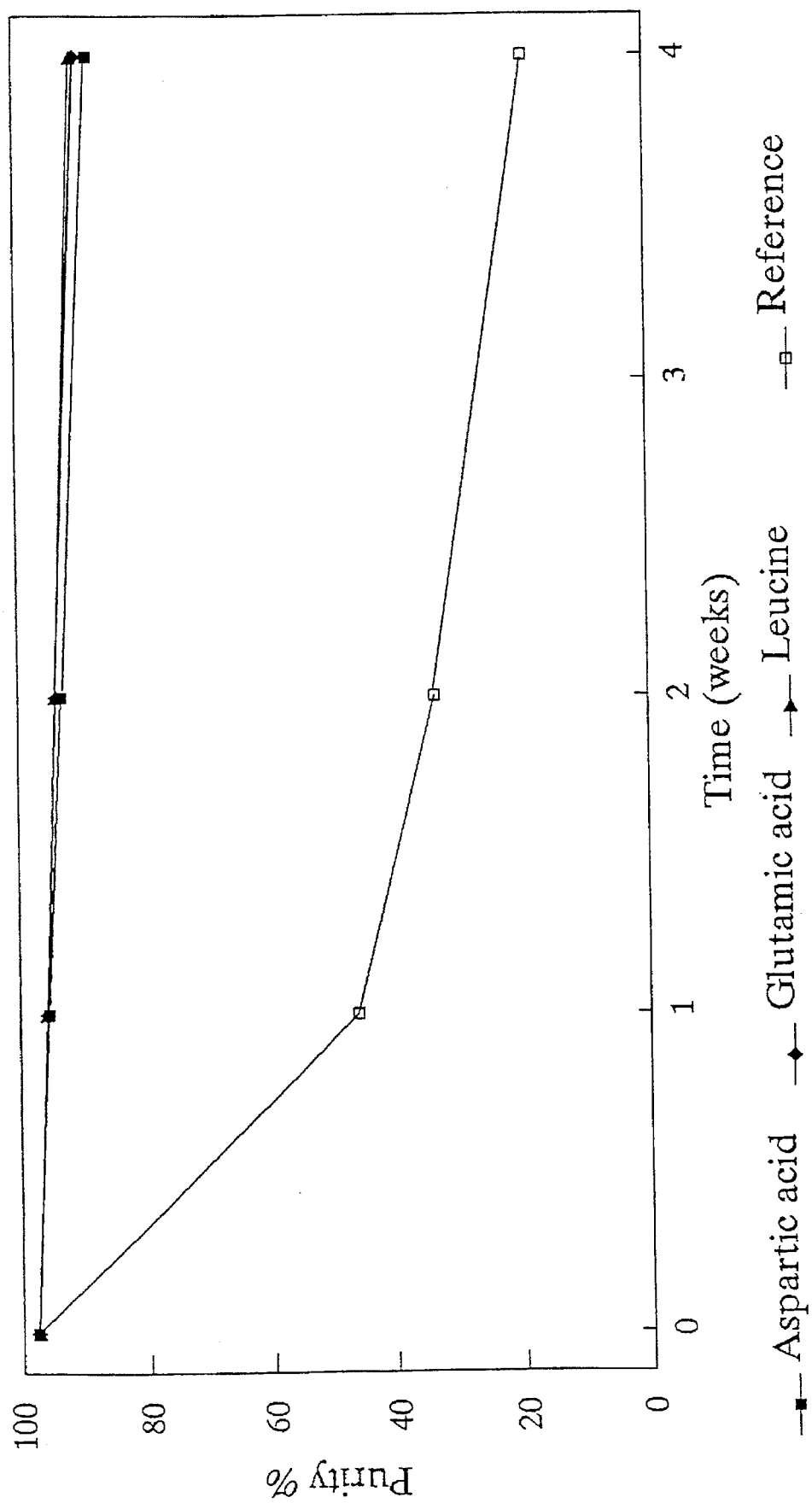
FIG. 5 shows the decomposition of glucagon stabilized with 10 mM Aspartic Acid, Glutamic Acid or Leucine as compared with the corresponding formulation without addition of amine acid as a function of the time.
Figure 6:
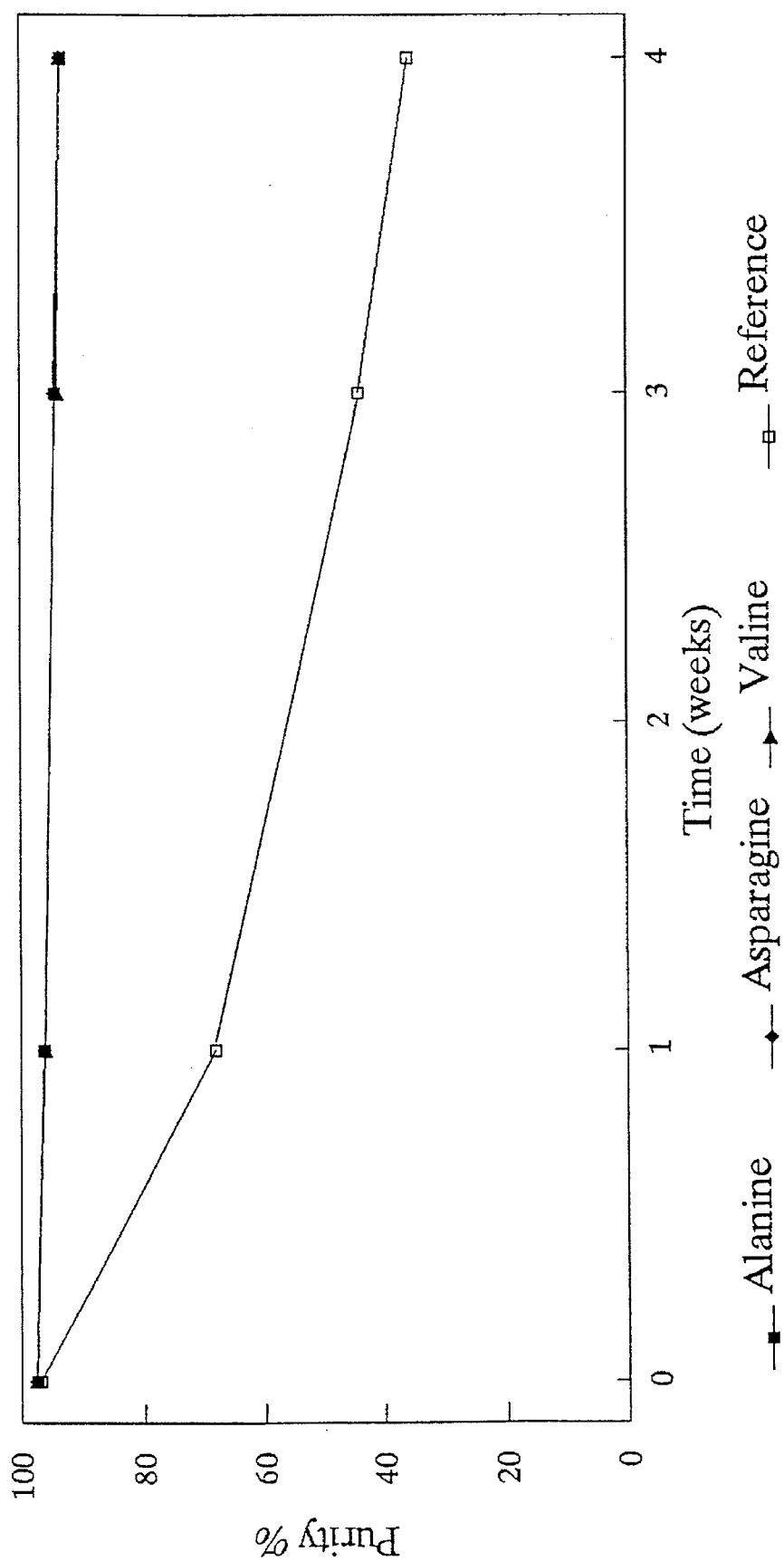
FIG. 6 shows the decomposition of glucagon stabilized with 10 mM Alanine, Asparagine or Valine as compared with the corresponding formulation without addition of amine acid as a function of the time.
Figure 7:
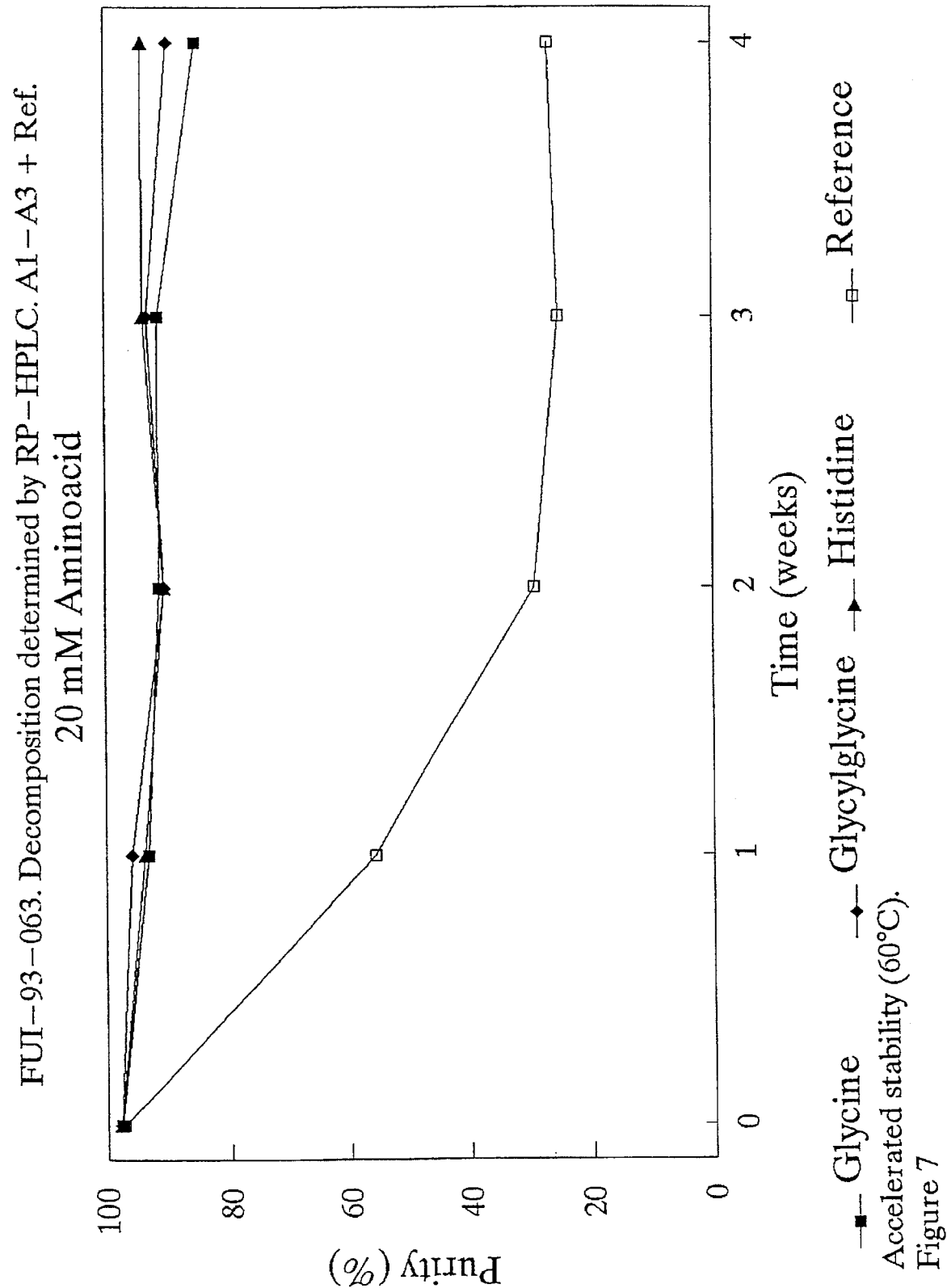
FIG. 7 shows the decomposition of glucagon stabilized with 20 mM Glycine, Glycylglycine or Histidine as compared with the corresponding formulation without addition of amine acid as a function of the time.
Figure 8:
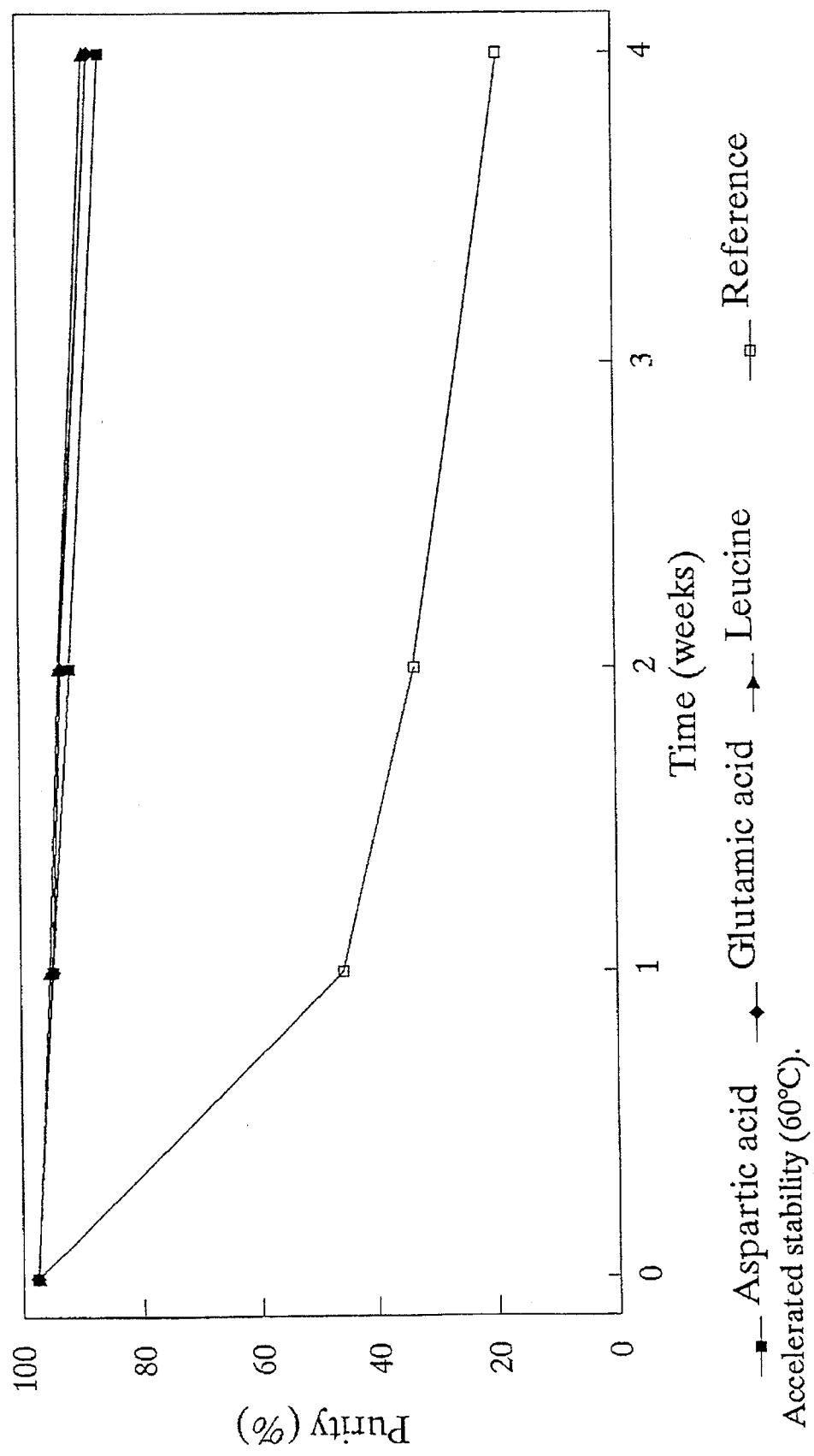
FIG. 8 shows the decomposition of glucagon stabilized with 20 mM Aspartic Acid, Glutamic Acid or Leucine as compared with the corresponding formulation without addition of amine acid as a function of the time.

The test formulations were incubated at 60° C., for a total period of 4 weeks. The degradation of the formulations were measured weekly by reverse phase HPLC. The results are shown in Table 1 and FIGS. 1–9.

The results show that a very pronounced stabilization of glucagon is obtained by adding stabilizing agent in accordance with the invention.

TABLE 1

| Week | Conc. AA (mM) | Glycine RPC % | Glycylglycine RPC % | Histidine RPC % | Reference RPC % |
| --- | --- | --- | --- | --- | --- |
| 0 | 5 | 98.00 | 97.90 | 97.90 | 97.60 |
| | 10 | 97.90 | 97.90 | 98.00 | |
| | 20 | 97.80 | 97.90 | 97.90 | |
| 1 | 5 | 97.10 | 96.40 | 94.70 | 55.80 |
| | 10 | 92.40 | 97.00 | 97.20 | |
| | 20 | 93.40 | 96.10 | 94.00 | |
| 2 | 5 | 91.60 | 95.20 | 91.20 | 29.30 |
| | 10 | 94.50 | 93.70 | 94.40 | |
| | 20 | 91.60 | 90.80 | 90.90 | |

TABLE 1-continued

| Week | Conc. AA (mM) | Glycine RPC % | Glycylglycine RPC % | Histidine RPC % | Reference RPC % |
|---|---|---|---|---|---|
| 3 | 5 | 94.80 | 95.30 | 88.10 | 25.30 |
|   | 10 | 93.20 | 94.30 | 87.60 | |
|   | 20 | 91.80 | 93.60 | 94.10 | |
| 4 | 5 | 84.60 | 91.70 | 90.90 | 26.90 |
|   | 10 | 93.30 | 87.50 | 93.30 | |
|   | 20 | 85.40 | 90.10 | 94.20 | |

TABLE 2

| Week | Conc. AA (mM) | Aspartic acid RPC % | Glutamic acid RPC % | Leucine RPC % | Reference RPC % |
|---|---|---|---|---|---|
| 0 | 5 | 97.70 | 97.10 | 97.70 | 97.80 |
|   | 10 | 97.80 | 97.70 | 97.60 | |
|   | 20 | 97.70 | 97.70 | 97.60 | |
| 1 | 5 | 72.70 | 60.30 | 81.00 | 45.80 |
|   | 10 | 95.60 | 95.80 | 95.90 | |
|   | 20 | 94.80 | 94.90 | 95.40 | |
| 2 | 5 | 65.80 | 48.10 | 74.70 | 33.50 |
|   | 10 | 93.30 | 94.10 | 94.20 | |
|   | 20 | 91.90 | 93.30 | 93.60 | |
| 3 | 5 | | | | |
|   | 10 | | | | |
|   | 20 | | | | |
| 4 | 5 | 57.80 | 32.70 | 67.00 | 19.20 |
|   | 10 | 88.60 | 90.50 | 91.00 | |
|   | 20 | 86.50 | 88.20 | 89.10 | |

TABLE 3

| Week | Conc. AA (mM) | Alanine RPC % | Asparagine RPC % | Valine RPC % | Reference RPC % |
|---|---|---|---|---|---|
| 0 | 5 | 97.30 | 97.30 | 97.40 | 97.00 |
|   | 10 | 97.50 | 97.60 | 97.60 | |
|   | 20 | 97.30 | 97.60 | 97.30 | |
| 1 | 5 | 93.60 | 93.90 | 85.90 | 68.10 |
|   | 10 | 96.30 | 96.20 | 96.10 | |
|   | 20 | 95.90 | 96.00 | 95.80 | |
| 2 | 5 | | | | |
|   | 10 | | | | |
|   | 20 | | | | |
| 3 | 5 | 90.90 | 91.90 | 80.00 | 44.00 |
|   | 10 | 94.30 | 94.40 | 94.00 | |
|   | 20 | 93.20 | 93.80 | 92.80 | |
| 4 | 5 | 89.90 | 91.40 | 75.40 | 35.90 |
|   | 10 | 93.40 | 93.60 | 93.50 | |
|   | 20 | 92.30 | 93.00 | 92.10 | |

We claim:

1. A pharmaceutical preparation comprising glucagon and a stabilizing amount of a pharmaceutically acceptable ampholyte, wherein the ampholyte is selected from the group consisting of glycine, ethylglycine, glycylglycine, trimethylglycine, alanine, β-alanine, valine, leucine, norleucine, isoleucine, serine, threonine, aspartic acid, glutamic acid, hydroxyglutamic acid, lysine, hydroxylysine, ornithine, arginine, methionine, asparagine, glutamine, taurine, creatinine, and ethylenediaminetetraacetic acid.

2. The pharmaceutical preparation according to claim 1, wherein the ampholyte is a pharmaceutically acceptable naturally occurring amino acid or a dipeptide or a mixture thereof.

3. The pharmaceutical preparation according to claim 2, wherein the amino acid or dipeptide is an amino acid selected from the group consisting of glycine, glycylglycine, or a mixture thereof.

4. The pharmaceutical preparation according to claim 1, further comprising a pharmaceutical acceptable excipient.

5. The pharmaceutical preparation according to claim 4, wherein the excipient is one or more compounds selected from the group consisting of disaccharides, sugar alcohols, polysaccharides, and polyvalent alcohols.

6. The pharmaceutical preparation according to claim 4, wherein the excipient is present in an amount 10 to 600 micromoles per mg glucagon.

7. The pharmaceutical preparation according to claim 3, wherein the glycine or glycylglycine is present in an mount from 0.01 to 50 micromoles per mg glucagon.

8. The pharmaceutical preparation according to claim 1, wherein the pH is adjusted to a value in the interval 2–7.

9. A method for the preparation of a pharmaceutical preparation according to claim 1, comprising (a) dissolving glucagon in a solution which comprises the ampholyte and optionally an excipient, and (b) lyophilizing the pharmaceutical preparation.

10. The pharmaceutical preparation according to claim 5, wherein the disaccharide one of lactose, trehalose, or sucrose, the sugar alcohol is sorbitol or mannitol, the polysaccharide is Dextran or Ficoll, and the polyvalent alcohol is polyethylene glycol or polyvinyl alcohol.

11. The pharmaceutical preparation according to claim 7, wherein the glycine, or glycylglycine is present in an amount about 10 micromoles per mg glucagon.

12. The pharmaceutical preparation according to claim 8, wherein the pH is adjusted to between 2.3 to 3.8.

13. The pharmaceutical preparation according to claim 12, wherein the pH is adjusted to 2.8..

\* \* \* \* \*